United States Patent
Hong (10) Patent No.: US 12,062,438 B1
(45) Date of Patent: Aug. 13, 2024

(54) METHOD AND SYSTEM FOR AUTOMATING STANDARD API SPECIFICATION FOR DATA DISTRIBUTION BETWEEN HETEROGENEOUS SYSTEMS

(71) Applicant: LEMONHEALTHCARE LTD, Seoul (KR)

(72) Inventor: Byung Jin Hong, Seoul (KR)

(73) Assignee: LEMONHEALTHCARE LTD, Seoul (KR)

( * ) Notice: Subject to any disclaimer, the term of this patent is extended or adjusted under 35 U.S.C. 154(b) by 0 days.

(21) Appl. No.: 18/292,964

(22) PCT Filed: Apr. 20, 2022

(86) PCT No.: PCT/KR2022/005657
§ 371 (c)(1),
(2) Date: Jan. 29, 2024

(87) PCT Pub. No.: WO2023/017953
PCT Pub. Date: Feb. 16, 2023

(30) Foreign Application Priority Data

Aug. 13, 2021 (KR) .................. 10-2021-0107257

(51) Int. Cl.
*G16H 40/20* (2018.01)
*H04L 67/02* (2022.01)
*H04L 67/10* (2022.01)

(52) U.S. Cl.
CPC ............ *G16H 40/20* (2018.01); *H04L 67/02* (2013.01); *H04L 67/10* (2013.01)

(58) Field of Classification Search
None
See application file for complete search history.

(56) References Cited

U.S. PATENT DOCUMENTS 8,533,746 B2 * 9/2013 Nolan .................... G16H 10/60
726/4
2016/0092344 A1 * 3/2016 Bally .................. G06F 11/3664
717/124

(Continued)

FOREIGN PATENT DOCUMENTS

JP 2021068067 A 4/2021
KR 101719926 B1 3/2017

(Continued)

OTHER PUBLICATIONS

Ingenerf, Josef, Jörg Reiner, and Bettina Seik. "Standardized terminological services enabling semantic interoperability between distributed and heterogeneous systems." International journal of medical informatics 64.2-3 (2001): 223-240. (Year: 2001).*

(Continued)

*Primary Examiner* — Katherine Kolosowski-Gager
*Assistant Examiner* — Ashley Elizabeth Evans
(74) *Attorney, Agent, or Firm* — NKL Law; Byungwoong Park (57) ABSTRACT

A method for automating a standard API specification for data distribution between heterogeneous systems. The method includes steps of learning a standard API and automating a standard API specification. The learning a standard API comprises the steps: defining a standard API specification, standard terms, and parameters; requesting, by a cloud server, a hospital API specification from a hospital API server and receives a response of the hospital API specification from the hospital API server; receiving hospital and institutional API specifications and collects terms; analyzing the collected terms; mapping the analyzed terms; and mapping API parameters.

5 Claims, 5 Drawing Sheets

(56) References Cited

U.S. PATENT DOCUMENTS

2020/0401465 A1* 12/2020 Douglas ................. G16H 40/00
2023/0030187 A1*  2/2023 Shankar ................ G06F 9/5072

FOREIGN PATENT DOCUMENTS

| KR | 101878217 B1 | 7/2018 |
| KR | 101966752 B1 | 4/2019 |
| KR | 102139180 B1 | 7/2020 |
| KR | 102171436 B1 | 10/2020 |
| KR | 102226292 B1 | 3/2021 |
| KR | 20210045283 A | 4/2021 |
| KR | 102371078 B1 | 3/2022 |

OTHER PUBLICATIONS

International Search Report for PCT/KR2022/005657, dated Jul. 27, 2022.
Notice of Allowance of KIPO for Korean application No. 10-2021-0107257, issued on Feb. 8, 2022.
Office Action of KIPO for Korean application No. 10-2021-0107257, issued on Oct. 25, 2021.

* cited by examiner

METHOD AND SYSTEM FOR AUTOMATING STANDARD API SPECIFICATION FOR DATA DISTRIBUTION BETWEEN HETEROGENEOUS SYSTEMS

TECHNICAL FIELD

The present disclosure relates to a method and system for automating a standard API specification for data distribution between heterogeneous systems, and particularly to a method and system for automating a standard API specification for data distribution between heterogeneous systems by automatically mapping standard API parameters through artificial intelligence technology, thereby enabling data distribution without separate processing.

BACKGROUND ART

The majority of individuals lack the means to access and utilize their health information across various institutions, hindering their active participation in healthcare. According to the national public opinion survey of 2020, approximately 78% of respondents expressed willingness to use personal health information services, yet only 20.9% had actually utilized such services. Consequently, there is an urgent need to establish My Health Way (health information highway) that facilitates the convenient and efficient retrieval of health information scattered across multiple sources. If the My Health Way service becomes more widespread, the role of a platform for collecting and managing medical data is expected to emerge. Even in a case where an API specification is set as a standard for My Health data distribution, the need for medical institutions or demand sources to redevelop API programs to align with the standard could result in a significant investment of time and effort. Hence, there is a demand for providing an architecture and service that can convert and relay existing APIs to meet a standard specification so that participating institutions and related companies can reuse the existing APIs for data distribution, ensuring compatibility with various API specifications without the need for additional API development.

There is a related patent Korean Patent No. 10-1719926 (System and method for conversion between heterogeneous data stored through data collection API), but this related patent simply discloses conversion rules between data generated by different platforms and software for learning analysis, and a system for structural and semantic transformation of heterogeneous data.

SUMMARY

Technical Problems

According to one embodiment of the present disclosure, the present disclosure provides a method for automating a standard API specification for data distribution between heterogeneous systems by automatically mapping API parameters through artificial intelligence technology to map APIs of different hospitals to the standard.

Technical Solution

A method for automating a standard API specification for data distribution between heterogeneous systems according to the present disclosure is divided into learning a standard API and automating a standard API specification, and the learning of the standard API includes: defining, by an API definition unit of a cloud server, a standard API specification, standard terms, and parameters; requesting, by the cloud server, a hospital API specification from a hospital API server and receiving a response of the hospital API specification from the hospital API server; collecting, by a data collection module of an API learning unit of the cloud server, terms by receiving hospital and institution API specifications; analyzing the collected terms by a term analysis module of the API learning unit of the cloud server; mapping the analyzed terms by a term mapping module of the API learning unit of the cloud server; and mapping API parameters by a decision processing module of the API learning unit of the cloud server.

Effect of Invention

According to the present disclosure, it is possible to automate mapping tasks based on a standard API specification between hospitals, insurance companies, etc. through artificial intelligence technology instead of humans.

In addition, it is possible to provide an architecture and service that can convert and relay existing APIs to a standard specification, enabling participating institutions and related companies to reuse existing APIs for data distribution.

In addition, it is possible to provide services compatible with APIs of various specifications without additional API development.

DETAILED DESCRIPTIONS OF EXEMPLARY EMBODIMENTS

Specific structural and functional description of embodiments according to the concept of the present disclosure disclosed herein is exemplified only to describe the embodiments according to the concept of the present disclosure, and the embodiments according to the concept of the present disclosure may be implemented in various ways and are not limited to the embodiments described herein.

Embodiments described herein may be changed in various ways and various shapes, so specific embodiments are shown in the drawings and will be described in detail in this specification. However, it should be understood that the exemplary embodiments according to the concept of the present disclosure are not limited to the specific examples, but all modifications, equivalents, and substitutions are included in the scope and spirit of the present disclosure.

Terms used in the present disclosure are used only in order to describe specific exemplary embodiments rather than limit the present disclosure. Singular forms are intended to include plural forms unless the context clearly indicates otherwise. It will be further understood that the terms "comprises" or "have" used in this specification specify the presence of stated features, numbers, steps, operations, components, parts, or a combination thereof, but do not preclude the presence or addition of one or more other features, numerals, steps, operations, components, parts, or a combination thereof.

Hereinafter, embodiments of the present disclosure will be described in detail with reference to the drawings attached to this specification.

Figure 1:
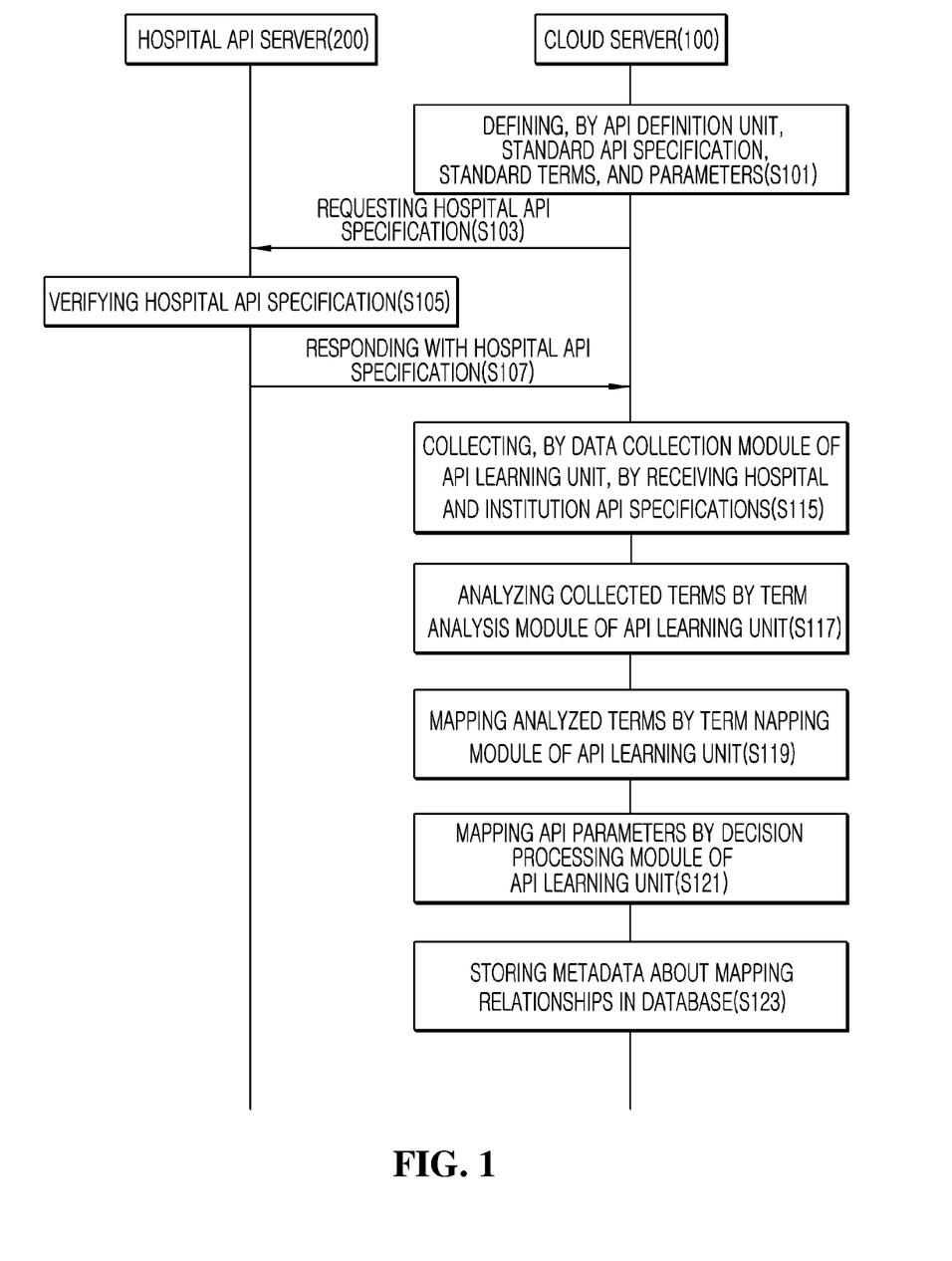
FIGS. 1 and 2 are flowcharts illustrating a method for automating a standard API specification for data distribution between heterogeneous systems according to an embodiment of the present disclosure.
Figure 2:
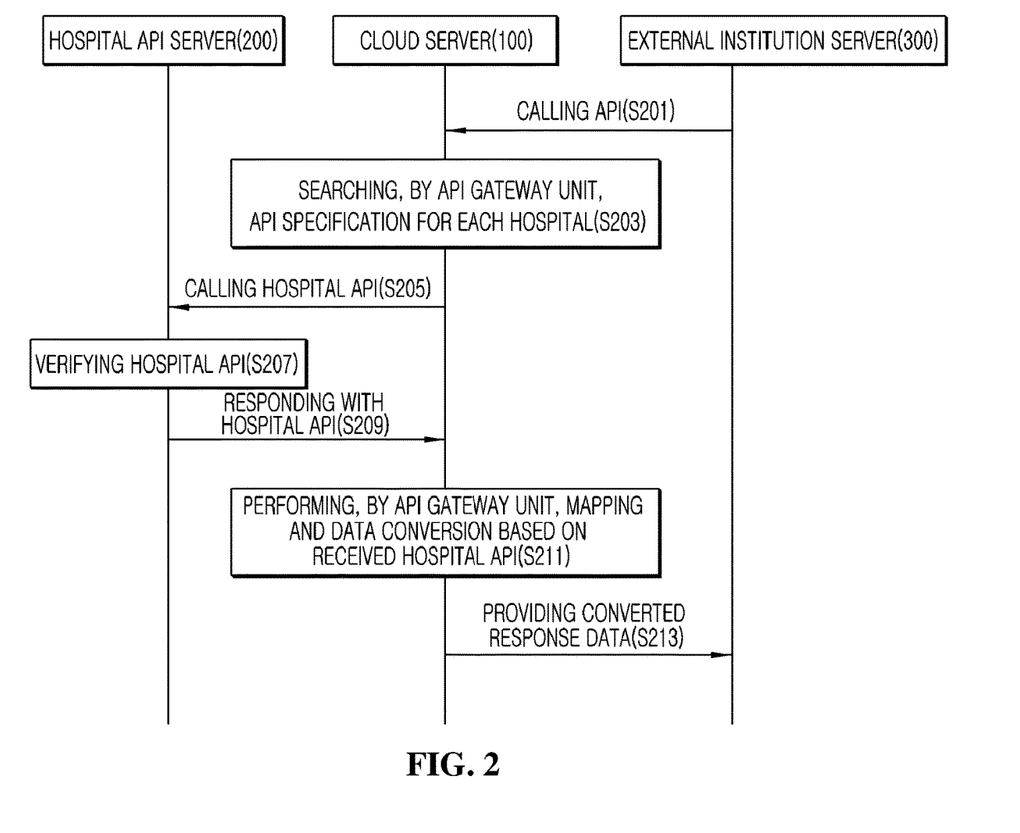

FIGS. 1 and 2 are flowcharts illustrating a method for automating a standard API specification for data distribution between heterogeneous systems according to an embodiment of the present disclosure.

Referring to FIGS. 1 and 2, the method for automating a standard API specification for data distribution between heterogeneous systems according to the present disclosure is divided into learning a standard API and automating a standard API specification.

FIG. 1 relates to a method for learning a standard API, and an API definition unit of a cloud server 100 defines a standard API specification, standard terms, and parameters (S101). The API definition unit may collect terms used in an API specification for each institution and define a relationship with terms to be mapped to the standard.

Then, the cloud server 100 requests a hospital API specification from a hospital API server 200 (S103), the hospital API server 200 verifies the hospital API specification (S105), and then the cloud server 100 receives a response of the hospital API specification from the hospital API server 200 (S107).

A data collection module of an API learning unit of the cloud server 100 collects terms by receiving the hospital API specification (S115). In some embodiments, it is possible to collect terms by receiving API specifications from external institutions other than hospitals. The data collection module may collect data on at least one of the following: technical terms, everyday terms, and abbreviations used by medical institutions and related companies, institutions, and organizations. In some embodiments, there may be a hospital API server that provides standard APIs, a hospital API server that provides the same data specification for each API but in a different order arrangement, or a hospital API for which a standard API specification can be extracted by combining two or more APIs.

A term analysis module of the API learning unit of the cloud server 100 analyzes the collected terms (S117). The term analysis module may break down combined terms used in API specifications into words. The term analysis module may analyze and classify combinations of words used in the terms used in the API specifications.

A term mapping module of the API learning unit of the cloud server maps the analyzed terms (S119). The term mapping module may map the analyzed terms to standard terms. The term mapping module may find a term used in a standard specification based on data received from the term analysis module. The term mapping module may derive a mapping rule for the found term from the accumulated learning data. If the term mapping module is unable to identify any established mapping rule, the decision processing module may process a new rule.

The decision processing module of the API learning unit of the cloud server maps API parameters (S121). The decision processing module may establish a relationship with parameters defined in the standard specification. The decision processing module may receive terms from the term mapping module and determine parameters that make up an API body defined in the standard API. The decision processing module may propose a new mapping relationship by learning terms that do not exist in predefined mapping relationship, and may add a mapping rule by saving the proposed new mapping relationship as a learning result according to the user's or administrator's response. If the decision processing module learns more rules for similar terms through learning, more mapping relationships with API specifications of various institutions may be established.

Metadata about the mapping relationships are stored in a database of the cloud server (S123). The database stores metadata about a standard API specification and terms, abbreviations, terms for AI learning, API specifications and terms used by institutions, and mapping relationships between standard APIs and institution APIs.

FIG. 2 relates to a method for automating a standard API specification, and when a cloud server 100 receives an API call from an external institution server 300 (S201), an API gateway unit searches for an API specification for each hospital (S203). In this case, the external institution server may be one of a medical institution server, a healthcare service company server, an insurance company server, a financial company server, or a medical-related institution server.

The cloud server calls a hospital API from a hospital API server, a hospital API server 200 verifies the hospital API, and then the cloud server receives a response of the hospital API from the hospital API server 200 (S209).

The API gateway unit of the cloud server performs mapping and data conversion based on the received hospital API (S211). The cloud server provides converted response data to the external institution server (S213). That is, in the present disclosure, a mapping task based on a standard API specification between institutions, such as hospitals and insurance companies, may be automated and provided through artificial intelligence technology instead of humans.

Figure 3:
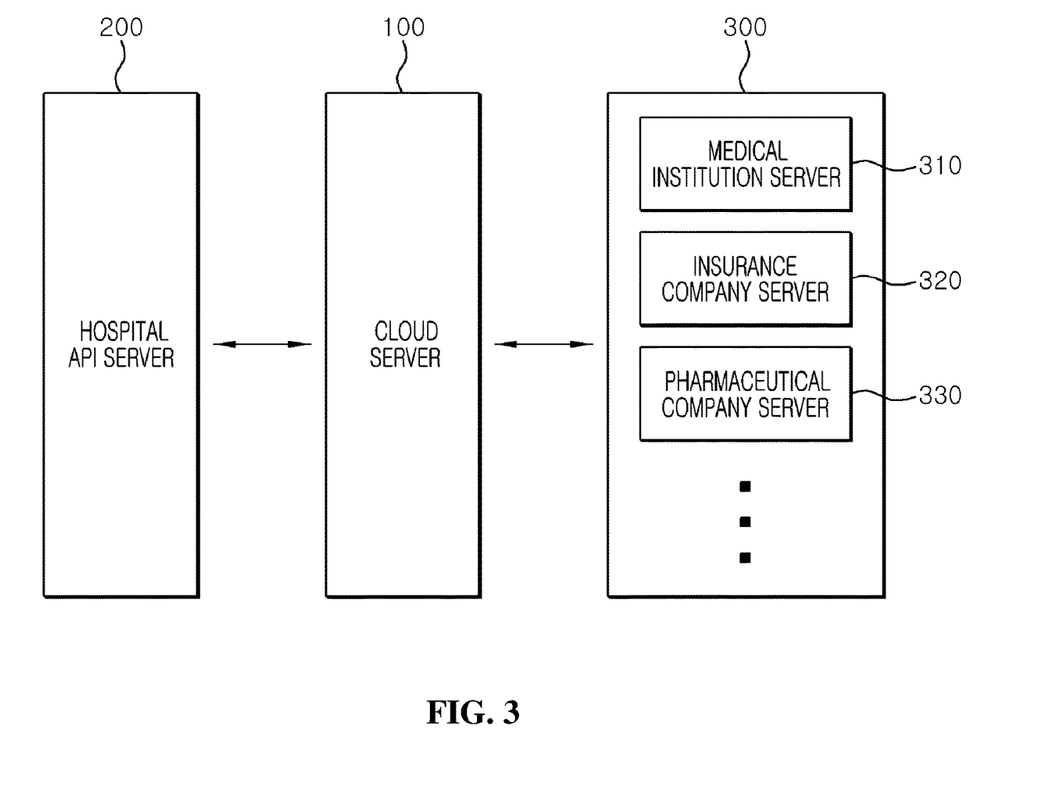
FIGS. 3 and 4 are diagrams illustrating a configuration of a system for automating a standard API standard for data distribution between heterogeneous systems according to an embodiment of the present disclosure.
Figure 4:
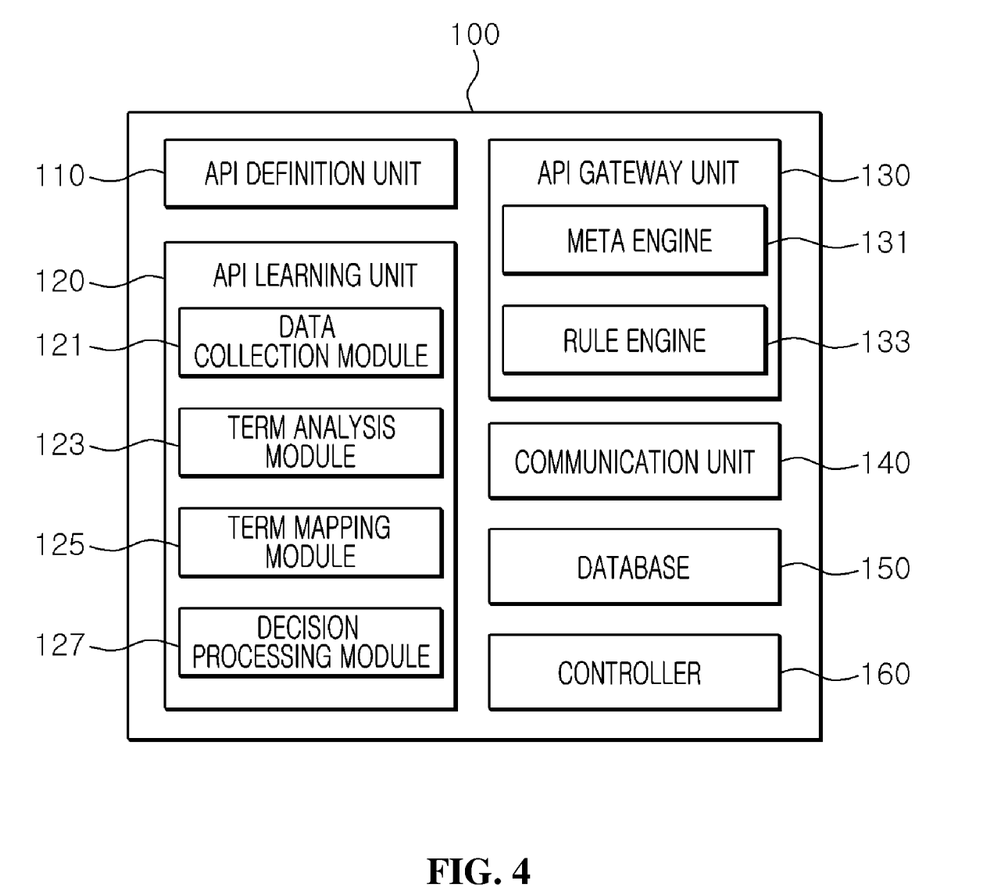

FIGS. 3 and 4 are diagrams illustrating a configuration of a system for automating a standard API standard for data distribution between heterogeneous systems according to an embodiment of the present disclosure.

Referring to FIG. 3, a system for automating a standard API specification is composed of a cloud server 100, a hospital API server 200, and an external institution server 300. The external institution server 300 includes a medical institution server 310, an insurance company server 320, and a pharmaceutical company server 330, and may be configured as any of various servers for data distribution according to embodiments.

Referring to FIG. 4, the cloud server 100 is composed of an API definition unit 110, an API learning unit 120, an API gateway unit 130, a communication unit 140, a database 150, and a controller 160.

The API definition unit 110 may define a standard API specification, standard terms, and parameters. The API definition unit 110 may collect terms used in an API specification for each institution and define a relationship with terms to be mapped to the standard.

The API learning unit 120 is composed of a data collection module 121, a term analysis module 123, a term mapping module 125, and a decision processing module 127.

The data collection module 121 may collect terms by receiving a hospital API specification. In some embodiments, the data collection module 121 may collect terms by receiving API specifications from external institutions other than the hospital. The data collection module 121 may collect data on at least one of the following: technical terms, everyday terms, and abbreviations used by medical institutions and related companies, institutions, and organizations.

The term analysis module 123 may analyze the terms collected by the data collection module. The term analysis module 123 may break down combined terms used in the API specifications into words. The term analysis module 123 may analyze and classify combinations of words used in the terms used in the API specifications.

The term mapping module 125 may map the terms analyzed by the term analysis module. The term mapping module 125 may map the analyzed terms to the standard terms. The term mapping module 125 may find a term used in a standard specification based on data received from the term analysis module. The term mapping module 125 may derive a mapping rule for the found term from the accumulated learning data. If the term mapping module 125 is unable to identify any established mapping rule, the decision processing module 127 may process a new rule.

The decision processing module 127 maps API parameters. The decision processing module 127 may establish a relationship with parameters defined in the standard specifications. The decision processing module 127 may receive a term from the term mapping module and determine parameters that make up an API body defined in the standard API. The decision processing module 127 may propose a new mapping relationship by learning terms that do not exist in predefined mapping relationships, and may add a mapping rule by saving the proposed new mapping relationship as a learning result according to the user's or administrator's response. If the decision processing module 127 learns more rules for similar terms through learning, more mapping relationships with API specifications of various institutions may be established.

The API gateway unit 130 is composed of a meta engine 131 and a rule engine 133. The API gateway unit 130 may perform API mapping and data conversion by reflecting a learning result in the meta engine 131 and rule engine 133. The meta engine 131 may receive different medical expense details from multiple hospitals and map the received medical expense details to a standard API for hospitals. For example, it is possible to receive and map medical expense details from multiple hospitals, categorized into medical treatment records, receipt details, itemized medical expense statements, prescription records, and prescription lists. The rule engine 133 generates an insurance claim document by invoking medical treatment records, detailed receipt items, itemized medical expense statements, prescription records, and prescription lists. The generated insurance claim document may be transmitted to the insurance company.

The communication unit 140 may transmit and receive data to and from the hospital API server 200 and the external institution server 300 by a wired or wireless communication module.

The database 150 may store metadata about mapping relationships. The database 150 may store metadata about a standard API specification and terms, abbreviations, terms for AI learning, API specifications and terms used by institutions, and mapping relationships between standard APIs and institution APIs.

The controller 160 may control each configuration of the cloud server 100. Operating software to control each configuration of the cloud server 100 may be installed to control the API definition unit, the API learning unit, the API gateway unit, the communication unit, and the database.

Figure 5:
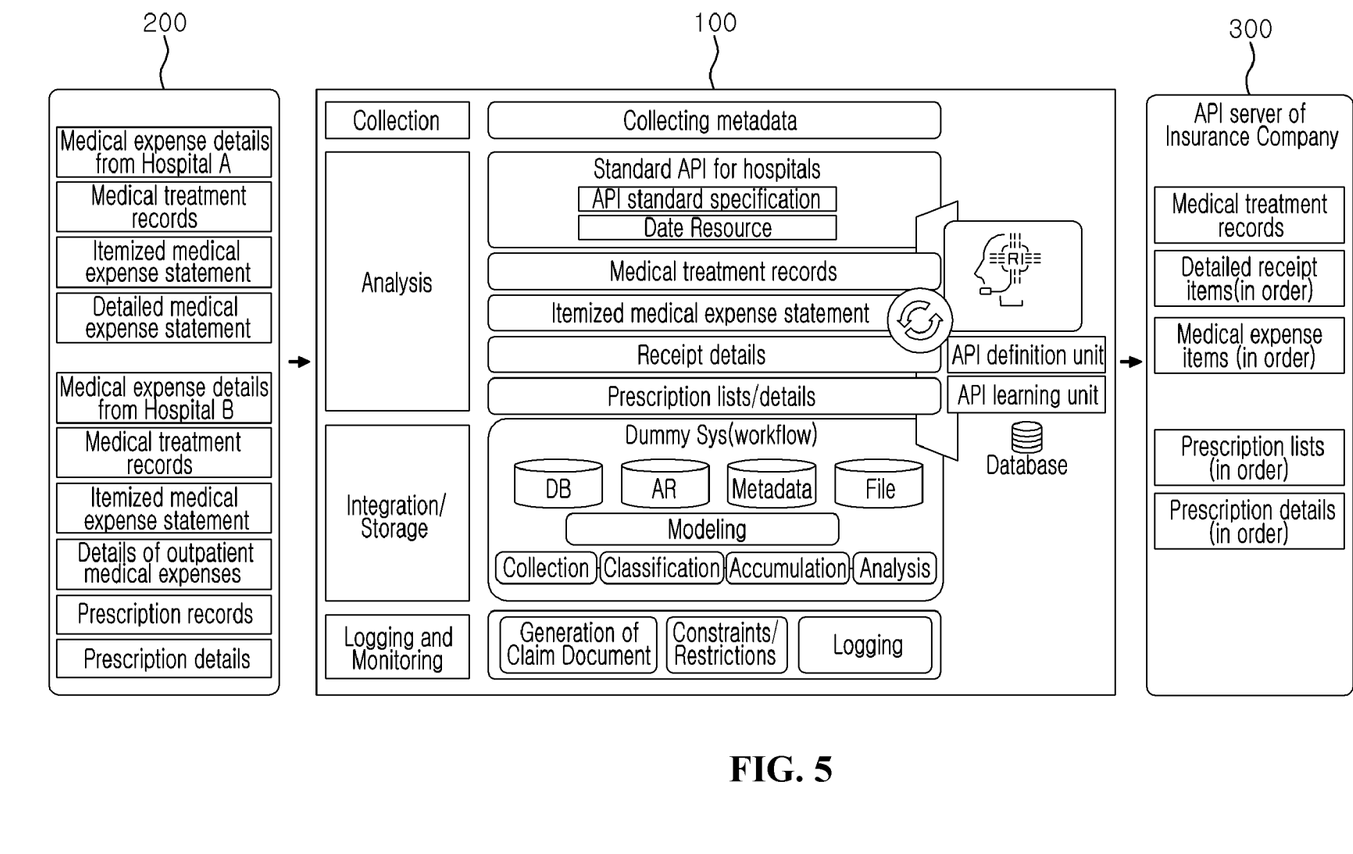
FIG. 5 is a diagram illustrating a configuration of a system architecture according to an embodiment of the present disclosure.

FIG. 5 is a diagram illustrating a configuration of a system architecture according to an embodiment of the present disclosure.

Referring to FIG. 5, the system architecture is composed of a hospital API server 100, a cloud server 200, and an external institution server 300 and configured as an architecture for collection, analysis, integration, storage, logging, and monitoring, which is associated with an API learning module of a cloud server when it comes to automatic mapping. This system architecture may include parameter-based workflow processing from the beginning to mid-to-long-term.

That is, in the present disclosure, API mapping and data conversion may be carried out by reflecting a learning result in the meta engine and rule engine of an API gateway unit, and continuous updates in data distribution may be performed.

Although the present disclosure has been described with reference to the exemplary embodiments illustrated in the drawings, those are only examples and may be changed and modified into other equivalent exemplary embodiments from the present disclosure by those skilled in the art. Therefore, the technical protective range of the present disclosure should be determined by the scope described in the claims.

What is claimed is:

1. A method for automating a standard API specification for data distribution between heterogeneous systems,
wherein the method is divided into learning a standard API and automating a standard API specification,
wherein the learning of the standard API comprises:
defining, by an API definition unit of a cloud server, a standard API specification, standard terms, and parameters;
requesting, by the cloud server, a hospital API specification from a hospital API server and receiving a response of the hospital API specification from the hospital API server;
collecting, by a data collection module of an API learning unit of the cloud server, terms by receiving hospital and institution API specifications;
analyzing the collected terms by a term analysis module of the API learning unit of the cloud server;
mapping the analyzed terms by a term mapping module of the API learning unit of the cloud server; and
mapping API parameters by a decision processing module of the API learning unit of the cloud server,
wherein the automating of the standard API specification comprises:
in response to the cloud server receiving an API call from an external institution server, searching for an API standard for each hospital by an API gateway unit;
calling, by the cloud server, a hospital API from a hospital API server and receiving a response of the hospital API from the hospital API server; and
performing mapping and data conversion by the API gateway unit of the cloud server based on the received hospital API,
wherein the API gateway unit is composed of a meta engine and a rule engine, the API gateway unit performs API mapping and data conversion by reflecting a learning result in the meta engine and rule engine, the meta engine receives different medical expense details from multiple hospitals and map the received medical expense details to a standard API for hospitals,
wherein the rule engine generates an insurance claim document by invoking medical treatment records, detailed receipt items, itemized medical expense statements, prescription records, and prescription lists, wherein the data collection module collects data on at least one of the following: technical terms, everyday terms, and abbreviations used by medical institutions and related companies, institutions, and organizations, wherein the term analysis module breaks down combined terms used in the API specifications into words, the term analysis module analyzes and classify combinations of words used in the terms used in the API specifications, wherein the term mapping module finds a term used in a standard specification based on data received from the term analysis module, the term mapping module derive a mapping rule for the found term from the accumulated learning data, if the term mapping module is unable to identify any established mapping rule, the decision processing module processes a new rule.

2. The method of claim 1, further comprising:
storing metadata about mapping relationships in a database of the cloud server.

3. The method of claim 1, further comprising:
providing, by the cloud server, converted response data to an external institution server.

4. The method of claim 1, wherein in performing the mapping and the data conversion based on the received hospital API by the API gateway unit of the cloud server, the standard API specification is automated even though the hospital API has same data specification for each API but in a different order arrangement.

5. A system for automating a standard API standard for data distribution between heterogeneous systems,
wherein the system is composed of a hospital API server, a cloud server, and an external institution server,
wherein the cloud server comprises:
an API definition unit configured to define the standard API specification, standard terms, and parameters;
an API learning unit comprising a data collection module for collecting terms by receiving hospital and institution API specifications, a term analysis module for analyzing the collected terms, a term mapping module for mapping the analyzed terms, and a decision processing module for mapping API parameters; and an API gateway unit configured to perform AIP mapping and data conversion based on a learning result, wherein the API gateway unit is composed of a meta engine and a rule engine, the API gateway unit performs API mapping and data conversion by reflecting a learning result in the meta engine and rule engine, the meta engine receives different medical expense details from multiple hospitals and map the received medical expense details to a standard API for hospitals, wherein the rule engine generates an insurance claim document by invoking medical treatment records, detailed receipt items, itemized medical expense statements, prescription records, and prescription lists, wherein the data collection module collects data on at least one of the following: technical terms, everyday terms, and abbreviations used by medical institutions and related companies, institutions, and organizations, wherein the term analysis module breaks down combined terms used in the API specifications into words, the term analysis module analyzes and classify combinations of words used in the terms used in the API specifications, wherein the term mapping module finds a term used in a standard specification based on data received from the term analysis module, the term mapping module derive a mapping rule for the found term from the accumulated learning data, if the term mapping module is unable to identify any established mapping rule, the decision processing module processes a new rule.

* * * * *